United States Patent [19]

Tabacchi

[11] 4,326,359
[45] Apr. 27, 1982

[54] DEVICE AND PROCESS FOR FRUIT TREE INSECT CONTROL

[76] Inventor: Frank E. Tabacchi, 4531 Cass Elizabeth, Pontiac, Mich. 48054

[21] Appl. No.: 181,979

[22] Filed: Aug. 28, 1980

[51] Int. Cl.³ .............................................. A01G 1/00
[52] U.S. Cl. ........................................ 47/58; 206/466; 206/534; 40/107; 434/276; 434/429; 116/308
[58] Field of Search ................... 47/58; 206/466, 534; 40/107; 434/429, 276; 116/308

[56] References Cited

U.S. PATENT DOCUMENTS

| | | | |
|---|---|---|---|
| 1,717,060 | 6/1929 | Mottayaw | 434/429 X |
| 3,099,352 | 7/1963 | Aven | 206/466 |
| 3,174,232 | 3/1965 | Beauvais | 434/276 |
| 3,432,951 | 3/1969 | Cherrin | 40/107 |
| 3,795,996 | 3/1974 | Hlavka | 40/107 |
| 4,148,273 | 4/1979 | Hollingsworth et al. | 206/534 |

Primary Examiner—Robert E. Bagwill
Attorney, Agent, or Firm—Basile, Weintraub & Hanlon

[57] ABSTRACT

A home gardener's process and device for fungus and insect control for fruit trees. The process employs the application of a variety of insecticides in a manner that avoids repetitious application of chemicals and forestalls the development of a resistant strain of insects. A variety of water soluble insecticides are prepackaged in measured amounts sufficient to mix with a gallon of water for the spray application of the mixtures to the fruit tree. The packets are numbered with indicia on the outer portion thereof indicating the sequence and the preferred timing of the application. The packets are numbered and arranged in their preferred order of application. The method for protection of pome fruit trees from fungus and insects includes twelve applications of four different chemicals over a prescribed sequence in a prescribed period of time. The method for protecting stone fruit trees from fungus and insects includes four additional applications of the chemicals or combinations of the chemicals following the initial twelve applications.

9 Claims, 1 Drawing Figure

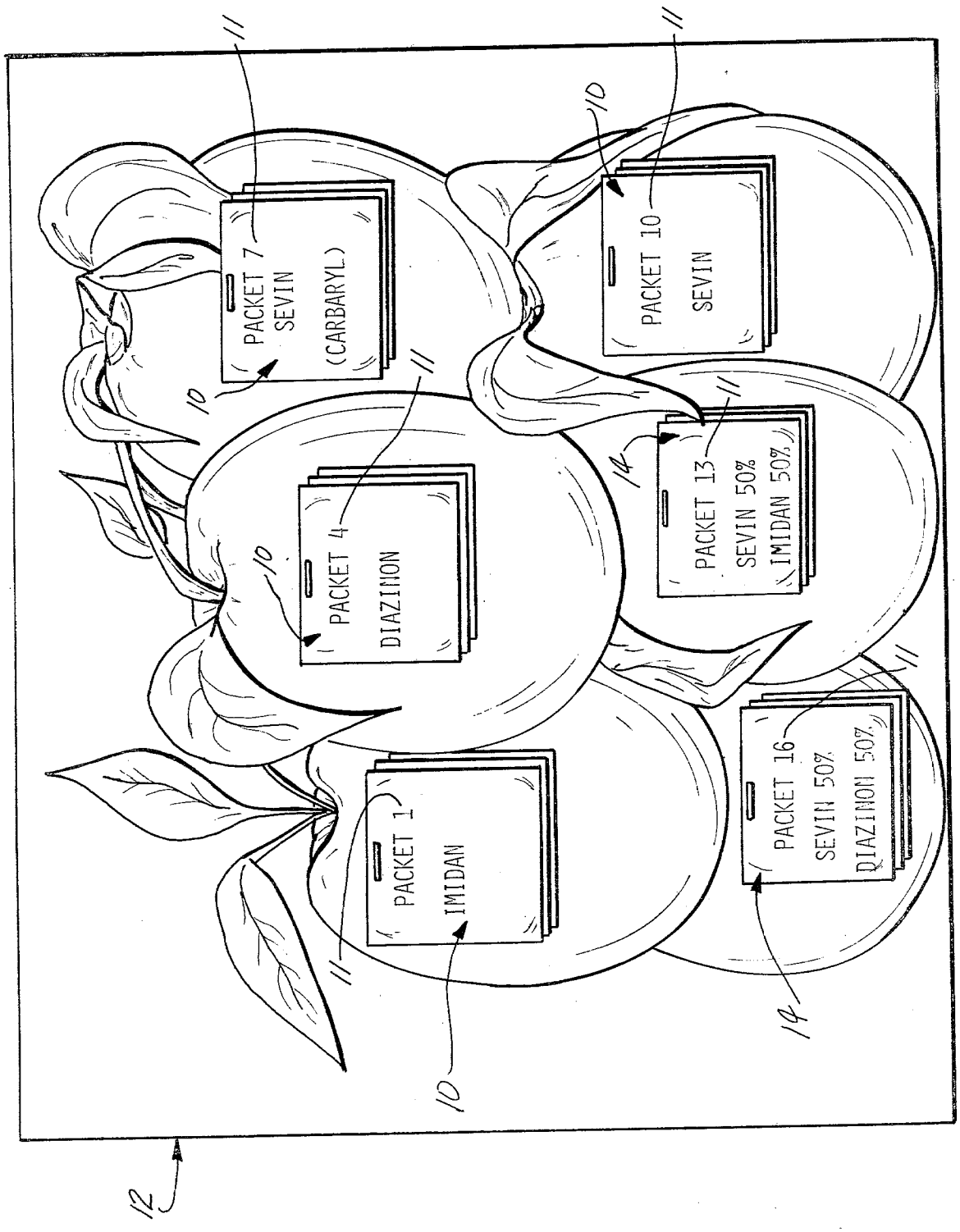

DEVICE AND PROCESS FOR FRUIT TREE INSECT CONTROL

BACKGROUND OF THE INVENTION

I. Field of the Invention

The present invention generally relates to the field of insect control and, in particular, the present invention is concerned with a device and method for protecting fruit trees from fungus and insects in a way that prevents the development of an insecticide-resistant insect.

II. Description of the Prior Art

In recent years there has been a deep concern by the public for a need to control insects in an ecologically responsible manner. Ecologists have shown that repetitious application of an insecticide can result in the development of a strain of insects resistant to the insecticide. Examples of methods and devices for destroying insects in the prior art are disclosed in U.S. Letters Pat. Nos. 454,117; 561,391; 1,948,228; and 3,192,666. These patents are relevant to the Applicant's invention in that they represent the closest prior art for protecting fruit trees against insects.

SUMMARY OF THE INVENTION

The present invention, which will be described in greater detail hereinafter, comprises a device and method for home gardeners to protect fruit trees for an entire season from fungus and insect infestation. The method involves the use of four chemicals deployed in a prescribed pattern and at prescribed times during the growing season for optimum protection. By rotating the application of the insecticides, thus avoiding repetitious applications of the same insecticide, the development of a insecticide-resistant insect is avoided.

In a preferred embodiment, twelve packets of the various insecticides are prepared in premeasured amounts with indicia on the outside of the packet instructing the user as to its contents and proper application. The packets are to be made available during the growing season by a garden store at the proper time for purchase and application by the home gardener.

It is therefore a primary object of the present invention to present for the home gardener's use a method of applying insecticide and fungicide to fruit trees that prevents the formation of a resistant strain of insects.

It is a further object of the present invention to provide such a system protecting fruit trees from disease that is easy and convenient for the home gardener to use.

It is yet another object of the present invention to provide the home gardener with a series of packets containing premeasured amounts of fungicide and insecticides for mixing with water and applying to fruit trees in a proper sequence.

It is yet a further object of the present invention to provide indicia on such packets to instruct the home gardener in the proper use of the contents of each packet.

Further objects, advantages, and applications of the present invention will become apparent to those skilled in the art of fruit growing when one example of the best mode contemplated for practicing the invention is read in conjunction with the accompanying drawing.

BRIEF DESCRIPTION OF THE DRAWING

The sole drawing is a decorative board on which are mounted a plurality of packets for use in the practice of the present invention.

DESCRIPTION OF THE PREFERRED EMBODIMENTS

Commercial fruit growers have for years known that spraying of trees with a variety of insecticides and mixing a combination of insecticides and fungicides is a more effective way of protecting the tree and also is the best way to reduce the possibility of an insecticide-resistant insect being developed. To follow the commercial grower's example, the backyard grower would be required to purchase and store a large variety of chemicals in much greater quantity than necessary for his/her use in order to rotate the use of insecticides. Furthermore, the amateur fruit grower lacks the expertise necessary to apply the insecticide in the preferred sequence without a great deal of study and research. The present invention addresses these problems by presenting for the backyard grower a prearranged series of packets of insecticide premeasured for his/her convenient use.

The present invention comprises a home grower's method for fungus and insect control for home fruit trees for the entire season which avoids the repetitious application of insecticides or pesticides and the possible development of a resistant strain of insects and comprises the steps of:

(a) mixing a premeasured amount of a wettable pesticide, such as a phthalimide, for example N-(mercaptomethyl)phthalimide-S-(o,o-dimethylphosphorodithioate) powder to a predetermined amount of water to form an aqueous solution thereof and spraying the tree when leaf buds show green. The phthalimide is a commercially available product such as that sold commercially under the name IMIDAN. In its commercial form, the product is available as a 50%—50% weight mixture with inert ingredients.

(b) About ten days after step (a), an aqueous solution is prepared by mixing a premeasured amount of a wettable fungicide to a predetermined amount of water and spraying the tree therewith. The fungicide contemplated for use herein is a 50%—50% weight mixture of CAPTAN and has an active ingredient N-[(trichloromethyl)thio]-4-cyclohexene-1,2-dicarboximide. The fungicide is sold commercially under the name CAPTAN power.

(c) Next, the same wettable aqueous solution of the fungicide of step (b) is sprayed onto the tree when the fruit buds begin to open.

(d) Thereafter a premeasured amount of a phosphorothioate powdered pesticide is mixed with a predetermined amount of water. This aqueous solution is then sprayed on after three-fourths of the petals have dropped. The phosphorothioate is preferably, o,o-diethyl-o-(2-isopropyl-6-methyl-4-pyrimidinyl)phosphorothioate. This compound is commercially available as a 50%—50% weight mixture thereof with an inert ingredient which promotes wettability. The compound is sold commercially under the name DIAZINON.

(e) Approximately ten days after three-fourths of the petals have dropped, the tree is sprayed with an aqueous solution of the phthalimide pesticide, as defined above.

(f) Approximately ten days following step (e) and when no atmospheric rain is present, the tree is sprayed with an aqueous solution similar to that defined in step (d).

(g) Approximately ten days following step (f) and when no rain is predicted, the tree is sprayed with a third pesticide. This third pesticide is a carbaryl pesticide. It is commercially available under the name SEVIN as a powder comprising an 80-20 weight mixture of carbaryl (1-naphtyl-N-methylcarbamate) and inert ingredients, respectively. The pesticide is employed as an aqueous solution prepared by mixing the pesticide with a predetermined amount of water.

(h) The phosphorothiate and carbaryl pesticides are mixed with a predetermined amount of water. Then ten days following step (g) when there is no rain predicted, the tree is sprayed with this mixture.

(i) Approximately ten days following step (h) when there is no rain predicted an aqueous solution of the pesticide of step (a) defined above, is sprayed on the tree.

(j) Approximately ten days following step (i) when there is no rain predicted, the tree is sprayed with an aqueous solution of the third pesticide.

(k) Approximately ten days following step (j) when no rain has been predicted, an aqueous solution of the phosphorothioate, as defined in step (d) is sprayed on the tree.

(l) Lastly, approximately ten days following step (k) when no rain has been predicted, the tree is sprayed with an aqueous solution of the carbaryl pesticide.

In its commercially available forms, the preferred fungicide CAPTAN (50% wettable powder) is manufactured by the Chevron Chemical Co; DIAZINON (50% wettable powder) is manufactured by Ciba-Geigy; IMIDAN (50% wettable powder is manufactured by Stauffer Chemical Co; and SEVIN (Carbaryl) (80% wettable powder) is manufactured by F.M.C. (Food Machinery Corporation).

Each of the aqueous solutions are prepared by admixing approximately ½ ounces of dry material per one gallon of water. In the case of step (h) the mixture of pesticides is employed as ½ ounces of each pesticide in one gallon of water.

Application of the four chemicals in the order prescribed will provide control for the following pests:
1. Apple Maggot—Apple, Apricot
2. Codling Moth—Apple
3. Cutworms
4. Fruit Tree Leafroller—Apple, Pear, Tart Cherry, Sweet Cherry
5. Green Apple Aphid—all fruits
6. Green Fruitworm—Apple, Pear, Peach, Nectarine Apricot, Tart Cherry, Sweet Cherry
7. Oblique Banded Leafroller—Apple, Pear, Tart Cherry, Sweet Cherry
8. Plum Curculio—Apple, Peach, Nectarine, Apricot, Sweet Cherry
9. Red Banded Leafroller—Apple, Pear, Tart Cherry, Sweet Cherry
10. Rose Chafer—Tart Cherry, Sweet Cherry
11. Rose Apple Aphid—Peach, Nectarine
12. Rust Mite—all fruits
13. San Jose Scale (Crawler Stage)—Apple, Pear
14. Spotted Tentiform (Larvae Stage)—Apple
15. Tarnished Plant Bug—Apple, Pear, Peach, Nectarine.
16. White Apple Leafhopper—Apple, Peach, Tart Cherry, Sweet Cherry
17. Woolly Apple Aphid—all fruits The method outlined above will protect all varieties of apple trees and pear trees with the exception of the D-Anjou pear which should not be sprayed.

In the preferred embodiment, the chemicals are premeasured into packets with each packet numbered and labeled with the contents. These packets also contain indicia with instructions for mixing and for the time of application for each package.

For protection of stone fruit including peach, nectarine, apricot, sweet cherries, and tart cherries, four additional applications are required as follows:

(m) Approximately ten days following step (1) when no rain has been predicted, the tree is sprayed with an aqueous solution of the phthalimide and carbaryl pesticides. The aqueous solution is prepared by admixing a 1:1 weight mixture of the pesticides with a predetermined amount of water. Generally, about one half ounce of each pesticide per gallon of water is employed in preparing the aqueous solution.

(n) Repeating step (a) by spraying the tree approximately ten days following step (m) when no rain is predicted.

(o) Approximately ten days following step (n) when no rain has been predicted, step (h) is repeated.

(p) Approximately ten days following step (o) when no rain is predicted, step (g) is repeated.

Alternately, a dormant oil spray is applied to the tree prior to step (a) in early spring before the buds open and with twenty-four hours of above-freezing temperatures following.

It should also be noted that while phthalimide has been described comprising the first pesticide, phosphorothiate has been described as a second pesticide and carbaryl has been described as the third pesticide, the method of the present invention may also be effectively practiced by interchanging the various pesticides. Thus, the first pesticide may also consist of phosphorothiate or carbaryl, the second pesticide can be phthalimide or carbaryl and the third pesticide may be phthalimide or phosphorothiate. It is essential, however, when such an interchange of the insecticides is employed that at least two of the insecticides be interchanged so as to avoid repetitious application of the same insecticide over the entire steps of the method of the present invention.

Referring now to the drawing, in a preferred embodiment, a plurality of packets 10 are arranged in four groups of three packets each in consecutive order with each of the groups attached to a board 12 with decorative and informative indicia thereon. Each packet 10 is consecutively numbered, as shown by indicia 11. With the packets displayed in this manner, a home gardener can purchase a board which contains the necessary ingredients for a complete treatment of pome fruit for the entire season at a very economical and attractive price. For the treatment of stone fruit for a season, additional groups of packets 14 are attached to the board 12.

It can thus be seen that the present invention has provided a new and improved device and method for a complete spraying program for fruit trees for the backyard grower. The method of the present invention provides individual packets of premeasured fungicide and pesticides to treat a mature fruit tree for the entire growing season. Except for an early spring fungicide application, no two identical sprays are applied within a ten-day period. Use of the methods defined in the present application will reduce the possibility of the development of an insecticide-resistant or fungicide-resistance insect. The practice of the present invention eliminates the purchase and storing of excess chemicals and poisons by the amateur fruit grower and the possibility of damaging the ecology is substantially reduced.

While the practice of the invention is described herein above provides sufficient material to spray a dwarf fruit tree, it is obvious to the skilled gardener that larger trees or a larger number of trees may be treated using more than one packet or by the provision of packets to mix with more than one gallon of water.

Having thus described my invention, what I claim is:

1. A home gardener's method for fungus and insect control for pome fruit trees for an entire season avoiding repetitious application and the development of an insecticide resistant strain of insects using a first water soluble insecticide, a second water soluble insecticide, a third water soluble insecticide and a water soluble fungicide comprising the steps of:
   (a) mixing a pre-packaged amount of a first insecticide with a pre-determined amount of water to form an aqueous solution, and spraying a fruit tree with the aqueous solution when the tree leaf buds show green;
   (b) mixing a pre-packaged amount of a water soluble fungicide with a pre-determined amount of water to form an aqueous solution thereof and spraying the fruit tree ten days after step (a).
   (c) repeating the application of the aqueous fungicide solution of step (b) when the fruit buds begin to open;
   (d) mixing a pre-packaged amount of a second water soluble insecticide with a pre-determined amount of water and spraying the tree after three-fourths of the petals have dropped;
   (e) mixing a pre-packaged amount of the first water soluble insecticide with a pre-determined amount of water and spraying the tree approximately ten days following step (d);
   (f) spraying the tree approximately ten days following step (e) when no rain is predicted using an aqueous solution prepared as in step (d);
   (g) mixing a pre-packaged amount of a third water soluble insecticide with a pre-determined amount of water to form an aqueous solution and spraying the tree approximately ten days following step (b) when no rain is predicted;
   (h) mixing a pre-measured amount of the second insecticide and the third insecticide in a pre-determined amount of water to form an aqueous solution and spraying the tree with the aqueous solution approximately ten days following step (g) when no rain is predicted;
   (i) mixing a pre-measured amount of the first insecticide with a pre-determined amount of water to form an aqueous solution and spraying the tree with the aqueous solution approximately ten days following step (h) when no rain is predicted;
   (j) mixing a pre-packaged amount of the third insecticide with a pre-determined amount of water to form an aqueous solution and spraying the tree with the aqueous solution approximately ten days following step (i) when no rain is predicted;
   (k) mixing a pre-packaged amount of the second insecticide with a predetermined amount of water to form an aqueous solution and spraying the tree with the aqueous solution approximately ten days following step (j) when no rain is predicted; and
   (l) mixing a pre-packaged amount of the third insecticide with a pre-determined amount of water to form an aqueous solution and spraying the tree with the aqueous solution ten days following step (k) when no rain is predicted.

2. The home gardener's method for fungus and insect control as defined in claim 1 wherein the process protects stone fruit trees comprising the added steps of;
   (m) mixing a pre-packaged amount of the third water soluble insecticide with a pre-determined amount of water to form an aqueous solution and spraying the tree ten days following step (1) when no rain is predicted;
   (n) mixing a pre-packaged amount of the first water soluble insecticide with a pre-determined amount of water to form an aqueous solution and spraying the tree ten days following step (m) when no rain is predicted;
   (o) mixing a pre-packaged amount of the second water soluble insecticide and a pre-packaged amount of the third water soluble insecticide with a pre-determined amount of water to form an aqueous solution and spraying the tree with the aqueous solution approximately ten days following step (n) when no rain is predicted; and
   (p) mixing a pre-packaged amount of the third water soluble insecticide with a pre-determined amount of water to form an aqueous solution and spraying the tree with the aqueous solution approximately ten days following step (o) when no rain is predicted.

3. The home gardener's method for fungus and insect control as defined in claim 2 wherein the tree receives the added protection of a dormant oil spray preceding step (a) before the tree buds open with twenty-four hours of above-freezing temperatures following the dormant oil spray.

4. The home gardener's method for fungus and insect control as defined in claim 1 wherein:
   said first water soluble insecticide comprises -N-(mercaptomethyl) phthalimide-S-(o,o-dimethyl phosphorodithioate) as the active ingredient;
   said second water soluble insecticide comprises, -o,o-diethyl o-(2-isopropyl-6-methyl-4-pyrimidinyl) phosphorothioate as the active ingredient;
   said third water soluble insecticide comprises -carbaryl (1-naphthyl N-methylcarbamate) as the active ingredient; and
   said water soluble fungicide comprises -N[(trichloromethyl)thiol]-4-cyclohexene-1,2-dicarboximide.

5. The home gardener's method for fungus and insect control as defined in claim 1 wherein:
   said first water soluble insecticide comprises, o-,o-diethyl o-(2-isopropyl-6 methyl-4 pyrimidinyl) phosphorothioate as the active ingredient;
   said second water soluble insecticide comprises, -carbaryl (1-napthyl N-methylcarbamate) as the active ingredient;
   said third water soluble insecticide comprises -N-(mercaptomethyl) phthalimide S-(o,o-dimethyl phosphorodithioate) as the active ingredient; and
   said water soluble fungicide comprises -N[(trichloromethyl)thio]-4-cyclohexene-1,2dicarboximide.

6. The home gardener's method for fungus and insect control as defined in claim 1 wherein:

said first water soluble insecticide comprises, -carbaryl(1-naphthyl) N-methylcarbamate as the active ingredient;

said second water soluble insecticide comprises, -N-(mercaptomethyl) phthalimide-S-(o,o-dimethyl phosphorodithioate) as the active ingredient;

said third water soluble insecticide comprises -o,o-diethyl O-(2 isopropyl-6-methyl-4-pryimidinyl) phosphorothioate as the active ingredient; and said water soluble fungicide comprises -N-[(trichloromethyl)thio]-4-cyclohexene-1,2dicarboximide.

7. The home gardener's method for fungus and insect control as defined in claim 1 wherein the first water soluble insecticide is selected from the group consisting of:
- —N—(mercaptomethyl) phthalimide-S-(o,o-dimethyl phosphorodithioate) as the active ingredient;
- —o,o-diethyl o-(2-isopropyl-6-methyl-4-pryimidinyl) phosphorothioate as the active ingredient;
- -carbaryl (1-napthyl N-methylcarbamate) as the active ingredient; and mixtures thereof.

8. The home gardener's method for fungus and insect control as defined in claim 1 wherein the second water soluble insecticide is selected from the group consisting of:
- —N-(mercaptomethyl) phthalimide-S-(o,o-dimethyl phosphorodithioate) as the active ingredient;
- —o,o-diethyl o-(2-isopropyl-6-methyl-4-pyrimidinyl) phosphorothioate as the active ingredient;
- -carbaryl (1-napthyl N-methylcarbamate) as the active ingredient; and mixtures thereof.

9. The home gardener's method for fungus and insect control as defined in claim 1 wherein the third water soluble insecticide is selected from the group consisting of:
- -N-(mercaptomethyl) phthalimide-S-(o,o-dimethyl phosphorodithioate) as the active ingredient;
- -o-diethyl o-(2-isopropyl-6-methyl-4-pyrimidinyl) phosphorothioate as the active ingredient;
- -carbaryl (1-napthyl N-methylcarbamate) as the active ingredient; and mixtures thereof.

* * * * *